United States Patent
Maschke

(10) Patent No.: US 8,473,052 B2
(45) Date of Patent: Jun. 25, 2013

(54) IMPLANTABLE PACEMAKER

(75) Inventor: Michael Maschke, Lonnerstadt (DE)

(73) Assignee: Siemens Aktiengesellschaft, München (DE)

( * ) Notice: Subject to any disclaimer, the term of this patent is extended or adjusted under 35 U.S.C. 154(b) by 1863 days.

(21) Appl. No.: 11/311,772

(22) Filed: Dec. 19, 2005

(65) Prior Publication Data

US 2006/0142813 A1 Jun. 29, 2006

(30) Foreign Application Priority Data

Dec. 23, 2004 (DE) .................. 10 2004 062 399

(51) Int. Cl.
*A61N 1/37* (2006.01)

(52) U.S. Cl.
USPC .............................. 607/9; 128/908

(58) Field of Classification Search
USPC ...... 324/207.13, 236; 600/301, 466; 606/159; 607/3, 9, 61, 116, 122, 5
See application file for complete search history.

(56) References Cited

U.S. PATENT DOCUMENTS

| | | | | |
|---|---|---|---|---|
| 4,399,821 A * | 8/1983 | Bowers | .......................... | 600/301 |
| 4,611,127 A * | 9/1986 | Ibrahim et al. | ................ | 307/116 |
| 4,745,923 A * | 5/1988 | Winstrom | .......................... | 607/9 |
| 5,217,010 A * | 6/1993 | Tsitlik et al. | ....................... | 607/9 |
| 5,476,501 A * | 12/1995 | Stewart et al. | ................ | 607/127 |
| 5,541,507 A * | 7/1996 | Ekwall | ....................... | 324/207.13 |
| 5,620,463 A * | 4/1997 | Drolet | ................ | 607/3 |
| 6,161,040 A * | 12/2000 | Blunsden | .......................... | 607/5 |
| 6,209,764 B1 * | 4/2001 | Hartlaub et al. | ................ | 223/94 |
| 6,330,467 B1 | 12/2001 | Creighton, IV et al. | | |
| 6,772,001 B2 | 8/2004 | Maschke | | |
| 6,925,328 B2 * | 8/2005 | Foster et al. | ....................... | 607/9 |
| 2002/0019644 A1 * | 2/2002 | Hastings et al. | .............. | 606/159 |
| 2002/0133211 A1 * | 9/2002 | Weiner et al. | .................... | 607/61 |
| 2003/0083570 A1 * | 5/2003 | Cho et al. | ....................... | 600/410 |
| 2003/0083726 A1 | 5/2003 | Zeijlemaker et al. | | |
| 2003/0140931 A1 | 7/2003 | Zeijlemaker et al. | | |
| 2003/0176786 A1 | 9/2003 | Maschke | | |
| 2005/0003268 A1 * | 1/2005 | Scott et al. | ..................... | 429/176 |
| 2005/0065587 A1 * | 3/2005 | Gryzwa | ....................... | 607/122 |

FOREIGN PATENT DOCUMENTS

EP 0 030 953 B1 7/1981
EP 0 882 469 B1 12/1998

* cited by examiner

*Primary Examiner* — Carl H Layno
*Assistant Examiner* — Luther Behringer

(57) ABSTRACT

A pacemaker comprises an implantable pacemaker housing and a pacemaker electrode provided to transmit stimulation impulses, and a detector for a current which can be induced by an external magnetic field and flowing through the pacemaker electrode. A circuit element is provided to interrupt this inducible current.

13 Claims, 3 Drawing Sheets

IMPLANTABLE PACEMAKER

CROSS REFERENCE TO RELATED APPLICATION

This application claims priority of the German application No. 10 2004 062 399.6 DE flied Dec. 23, 2004, which is incorporated by reference herein in its entirety.

FIELD OF THE INVENTION

The invention relates to a pacemaker with an implantable pacemaker housing and a pacemaker electrode, which is provided to tot stimulation impulses to the heart.

BACKGROUND OF THE INVENTION

A pacemaker of this type is known for instance from EP 0 882 469 B1.

Implantable pacemakers are either operated using unipolar pacemaker electrodes or using bipolar pacemaker electrode. In the case of a unipolar electrode, the electro tip of the pacemaker electrode operates as a cathode and the pacemaker housing as an anode. The bipolar systems correspond to the unipolar systems insofar as they also operate using a cathodic electrode tip. Unlike unipolar systems, in the case of bipolar pacemaker electrodes, an anode is arranged however in the distal electrode region.

Complications can result both in the case of unipolar pacemaker electrodes as well as in the case of bipolar pacemaker electrodes, if the patient wearing the pacemaker is exposed to an intense magnetic field. Intense magnetic fields of up to 7 Tesla result particularly with magnetic resonance devices. If the magnetic field is changed, and/or the pacemaker electrode moves in the magnetic field, currents are induced which can cause the pacemaker electrode to heat up, thereby resulting in irreversible tissue damage. On this account, according to the prior art, patients with a pacemaker cannot be examined in magnetic resonance devices.

US 2003/0140931 A1 discloses a medical implantable system for reducing magnetic resonance effects, in which the electric circuit is interrupted as a function of a measured magnetic field, with the magnetic field being determined by means of a special magnetic field sensor.

SUMMARY OF THE INVENTION

The object of the invention is to reduce restrictions existing for a patient wearing a pacemaker during medical examinations.

This object is achieved according to the invention by means of an implantable pacemaker with the features of the claims. This comprises an implantable pacemaker housing and at least one pacemaker electrode, which is provided to transmit stimulation impulses to the heart. In order to at least attenuate currents induced in the pacemaker electrode by a magnetic field, at least one circuit element is provided which can interrupt the current flowing in the pacemaker electrode.

In this context a circuit element also includes a switch for the repeated opening and closing of an electric circuit and a component which only allows a one-off opening of a line, in particular a fuse. In a particularly simple embodiment, the pacemaker electrode is monitored by means of a blowout fuse, which fuses in the case of a current generated by an external magnetic field during the temperature increase resulting therefrom. In this case the patient requires a new electrode cable. The exchange of the pacemaker electrode is however related to a significantly lower exposure for the patient than potential effects by means of an intense magnetic field.

According to a preferred development, the circuit element which can interrupt the current flow through the pacemaker electrode, is configured as a reversible circuit element, i.e. a circuit element allowing a number of switching operations. A semiconductor circuit element is preferably used for this, in particular a transistor or thyristor technology. It is particularly advantageous to be able to switch the reversible circuit element via telemetry. The at least one circuit element can thus be opened from the outside of the patient before the patient is exposed to an intense magnetic field. After the circuit element has been opened, the stimulation impulses can however no longer be transmitted to the heart, but this is generally acceptable, since the patient is under medical supervision during the examinations undertaken, because of which the pacemaker is deactivated. The heart activity can be monitored for instance by ECG. If necessary, the heart activity can also be explicitly supported during the examination by means of medication.

In a variant which can be combined with the aforementioned embodiment, the reversible circuit element can be automatically switched as a function of the intensity of a magnetic field present. In this way the magnetic field can be measured for instance via the current induced in the pacer electrode. The triggering of the circuit element is preferably made noticeable by means of telemetry. The circuit element can be closed, in other words a reactivation of the pacemaker electrode after a preceding automatic shutdown, either automatically or after release by qualified medical personnel, preferably via telemetry, if the admissible limit value of a magnetic field is not reached. An automatically opening and re-closing circuit element can also operate in a temperature-dependent manner, for example as a bimetal circuit element.

The pacemaker preferably comprises only metallic components, which are non-ferromagnetic and is thus designed specially for intense magnetic fields. Provided an external magnetic field does not exceed an admissible limit value, the stimulation frequency of the pacemaker electrode in a preferred embodiment is not dependent on external magnetic fields. In contrast here, pacemakers according to the prior art can be partially explicitly influenced by external magnetic fields, in particular adjusted to a fixed stimulation frequency. These types of dependency of the mode of operation of the pacemaker on a magnetic signal are preferably controllable or generally not provided with pacemaker according to the invention, provided the limit value of the magnetic field admissible with the active pacemaker is not exceeded.

According to an advantageous embodiment the pacemaker electrode comprises a magnet, in particular electromagnet, which allows a targeted navigation of the pacemaker electrode controlled by an external magnetic field. A navigation system of this type is principally known for example from the US 2003/0176786 A1, U.S. Pat. No. 6,772,001 B2, and the US 2002/0019644 A1 and U.S. Pat. No. 6,330,467 B1.

The advantage of the invention is especially that with the aid of an electrode cable which can be interrupted by means of at least one circuit element, pacemaker patients which are not obliged, for medical reasons, to have the implanted pacemaker, operating continuously, can use diagnosis and treatment devices, in particular magnetic resonance devices, which have hitherto only been available to patients without pacemakers.

BRIEF DESCRIPTION OF THE DRAWINGS

An exemplary embodiment of the invention is described in more detail below with reference to a drawing, in which.

DETAILED DESCRIPTION OF THE INVENTION

Figure 1:
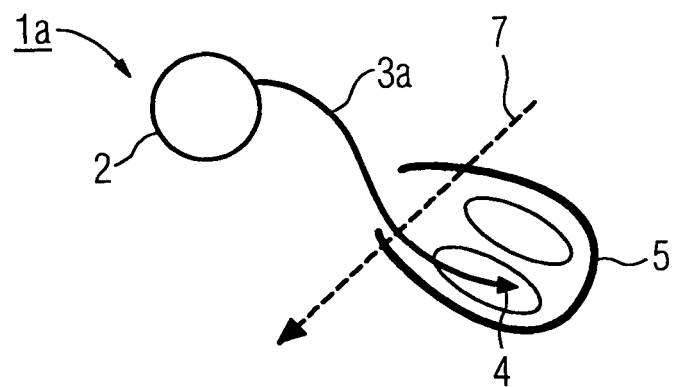
FIG. 1 shows a unipolar pacemaker according to the prior art

Parts or parameters corresponding to one another are provided in all the figures with the same reference characters.

Figure 2:
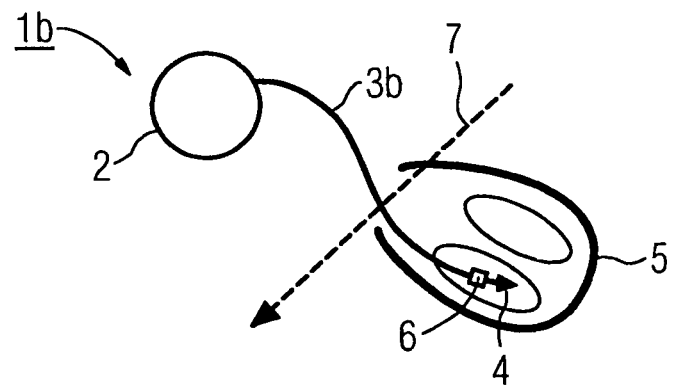
FIG. 2 shows a bipolar pacemaker according to the prior art

FIG. 1 and FIG. 2 show a greatly simplified unipolar pacemaker 1a and a bipolar pacemaker 1b, which each comprise a pacemaker housing 2 and a unipolar pacemaker electrode 3a and a bipolar pacemaker electrode 3b. The pacemaker electrode 3a and 3b is fixed in the ventricle of a heart by means of an electrode tip 4 sad is provided to transmit simulation impulses. As an alternative to the displayed embodiments, a number of pacemaker electrodes 3a and 3b can also be provided, which are guided to the atrium and to the ventricle.

In the bipolar system (FIG. 2), an anode ring 6 is arranged at a distance of approximately 2.5 cm from the electrode tip 4. The function of the anode is assumed in the unipolar system (FIG. 1) by the pacemaker housing 2. An external magnetic field 7 is indicated in both systems by a dashed arrow. If this increases to values which are too great, an electrical current can be induced in the pacemaker electrode 3a, 3b, said current representing a grave danger for the patient. For this reason patients with pacemaker systems according to FIGS. 1 and 2 cannot be examined using magnetic resonance devices.

Figure 3:
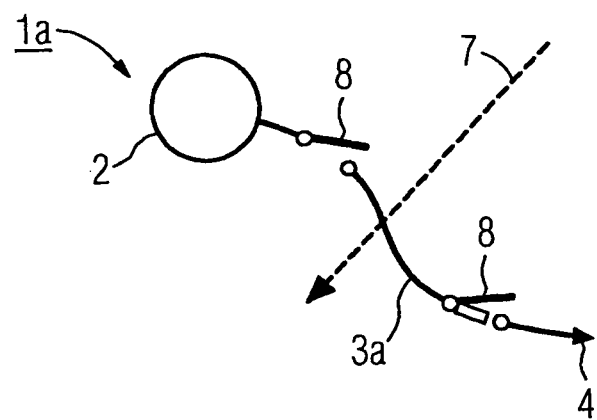
FIG. 3 shows a unipolar pacemaker according to the invention
Figure 4:
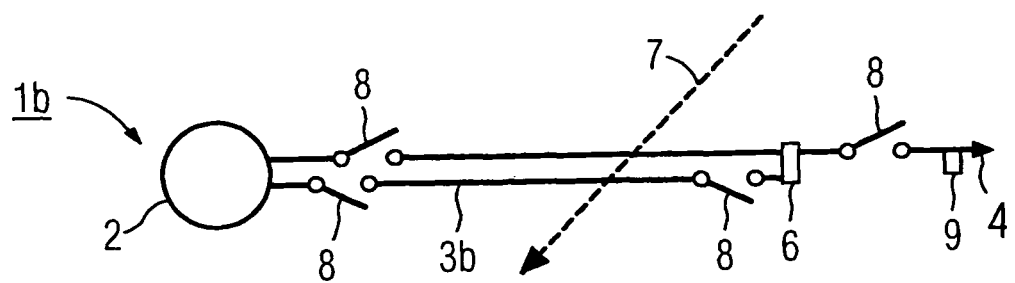
FIG. 4 shows a bipolar pacemaker according to the invention

FIGS. 3 and 4 show a symbolic representation in each instance of a pacemaker 1a, 1b according to the invention in a unipolar (FIG. 3) and a bipolar (FIG. 4) embodiment. The unipolar pacemaker electrode 3a according to FIG. 3 is thus equipped with two switches 8, the bipolar pacemaker electrode 3b according to FIG. 4 is equipped with four switches 8, generally also referred to as circuit elements. The switches 8 open once the magnetic field 7 exceeds a preferably adjustable limit value and thus protect the patient from dangerous exposure by means of induced currents. In the exemplary embodiment according to FIG. 4, an electromagnet is located in the region of the electrode tip, which, in conjunction with an external magnetic field, allows the pacemaker electrode 3b to be navigated in the body of the patient. A magnetic navigation of this type can be similarly realized with the exemplary embodiment according to FIG. 3. In both exemplary embodiments, a permanent magnet con be used in place of the electromagnet 9.

Figure 5:
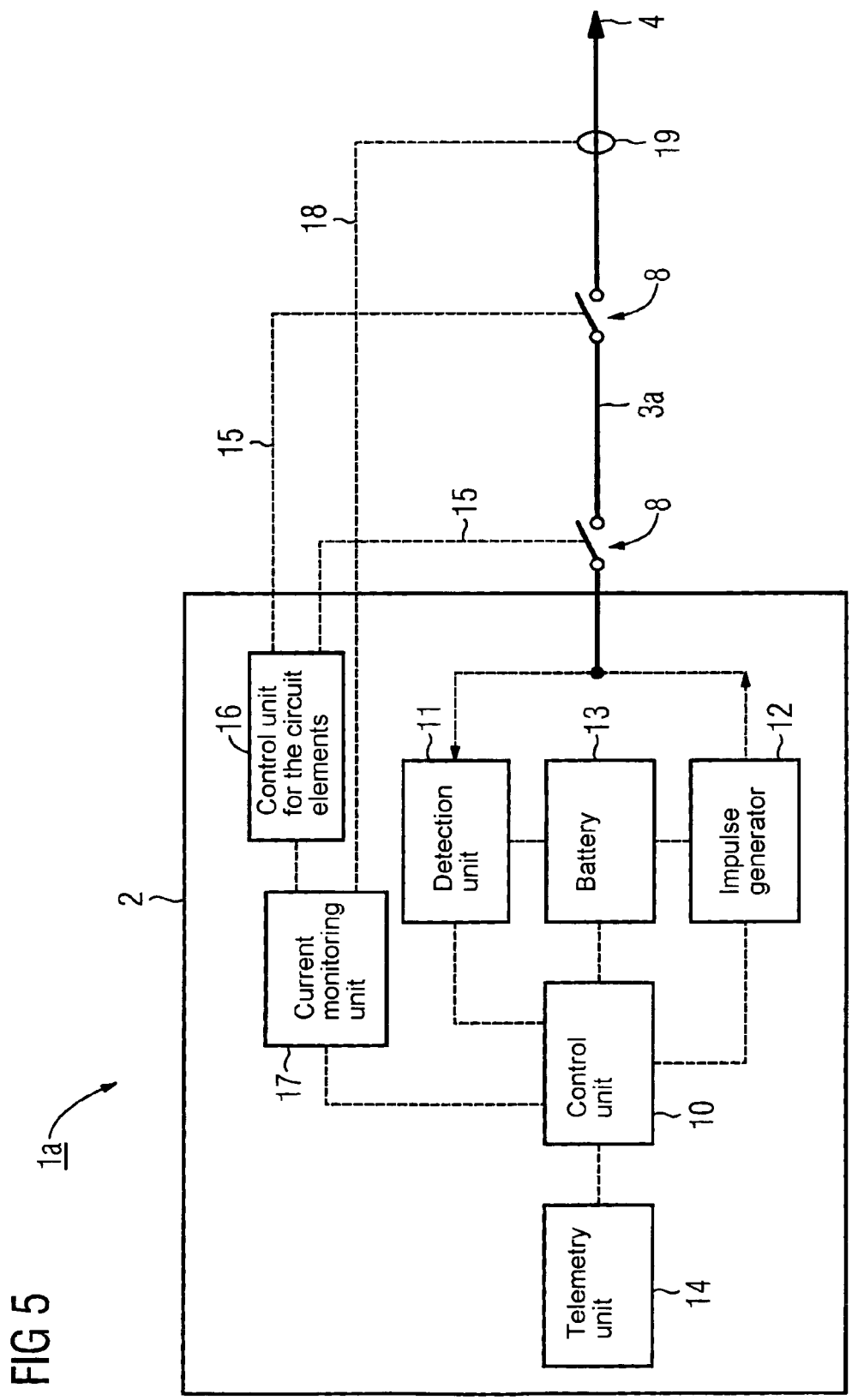
FIG. 5 shows a block diagram of the pacemaker according to FIG. 3

FIG. 5 shows a schematic representation of the structure of the pacemaker 1a according to FIG. 3. A control unit 10 is located in the pacemaker housing 2, which interacts with a detection unit 11, which serves to detect the signals (so-called sensing) outgoing from the heart 5, and interacts with an impulse generator 12 which generates the impulses to be transmitted to the pacemaker electrode 3. A battery 13 is provided for the power supply of the overall pacemaker 1a.

The pacemaker housing 2 further comprises a telemetry unit 14, which enables the status of the pacemaker 1a to be queried, and in particular enables the circuit element 8 to be switched from the outside of the patient. The circuit elements 8 are connected to a control unit 16 by means of control lines 15. This comprises an effective link with a current monitoring unit 17, to which a measuring element 19 is connected via a measuring line, said measuring element detects the induced current in the pacemaker electrode 3. A wireless signal transmission can also be provided instead of a wired signal transmission between different components of the pacemaker 1a. The components within the pacemaker housing 2 shown in FIG. 5 are similarly also located in the pacemaker 1b of the exemplary embodiment according to FIG. 4.

The invention claimed is:

1. A pacemaker, comprising:
an implantable pacemaker housing;
pacemaker circuitry positioned within the housing;
a pacemaker electrode lead extending from the housing for transmitting stimulation impulses; and
a detector for detecting current that is induced by an external magnetic field flowing through the pacemaker electrode lead; and
a circuit element positioned along the electrode lead and configured to isolate a portion of the electrode lead from a portion of the pacemaker circuitry and thereby interrupt induced current flowing through the electrode lead based on detection of current by the detector.

2. The pacemaker according to claim 1, characterized in that a blowout fuse is provided as the circuit element.

3. The pacemaker according to claim 1, wherein a reversible switch is provided as the circuit element.

4. The pacemaker according to claim 3, wherein a semiconductor circuit element is provided as the switch and a second circuit element is positioned along the electrode lead and configured to isolate a portion of the electrode lead from a portion of the pacemaker circuitry so that a segment of the electrode lead between the two circuit elements can be electrically isolated based on detection of current by the detector.

5. The pacemaker according to claim 3, wherein the switch can be controlled via telemetry.

6. The pacemaker according to claim 4, wherein the switch can be controlled via telemetry.

7. The pacemaker according to claim 3, wherein the switch is activated or de-activated as a function of magnetic field strength.

8. The pacemaker according to claim 3, wherein the switch activates or de-activates in a temperature-dependent manner.

9. The pacemaker according to claim 1, wherein the metallic components are non-ferromagnetic.

10. The pacemaker according to claim 1, wherein the detector controls the circuit element so that provision of a stimulation frequency by the pacemaker is not influenced by magnetic field strength when the switch is closed.

11. The pacemaker according to claim 1, wherein a magnet for navigating the pacemaker electrode lead in an external magnetic field is arranged on the pacemaker electrode lead.

12. The pacemaker according to claim 11, wherein an electromagnet is provided as the magnet.

13. The pacemaker according to claim 11, wherein a permanent magnet is provided as the magnet.

* * * * *